United States Patent [19]

Kraus et al.

[11] 4,233,434

[45] Nov. 11, 1980

[54] POLYAMIDE FROM AROMATIC PHOSPHORUS CONTAINING DIAMINE

[76] Inventors: Menahem A. Kraus, 14 Mordel Hagetaot St.; Moshe A. Frommer, 2a Eisenberg St., both of Rehovot; Mara Nemas, 28 Tamar St., Neve Monoson; Rodika Gutman, 77 Hashiloah St., Kiryat Sharet, all of Israel

[21] Appl. No.: 904,286

[22] Filed: May 9, 1978

Related U.S. Application Data

[63] Continuation-in-part of Ser. No. 652,812, Jan. 27, 1976.

[30] Foreign Application Priority Data

Jan. 27, 1975 [IL] Israel ......................................... 46510
Jul. 15, 1975 [IL] Israel ......................................... 47709

[51] Int. Cl.$^3$ ............................................. C08G 69/42
[52] U.S. Cl. ........................... 528/337; 210/500 M; 260/30.2; 260/30.6 R; 260/32.6 NA; 528/167; 528/220; 528/321
[58] Field of Search ................ 528/337, 321, 167, 220

[56] References Cited

U.S. PATENT DOCUMENTS

| | | | |
|---|---|---|---|
| 3,228,877 | 1/1966 | Mahon | 210/22 |
| 3,567,632 | 3/1971 | Richter et al. | 210/23 H |
| 3,686,116 | 8/1972 | Rio | 210/500 M |
| 3,822,202 | 7/1974 | Hoehn | 210/500 M |
| 3,825,493 | 7/1974 | Brown et al. | 210/23 H |
| 3,899,309 | 8/1975 | Hoehn et al. | 210/500 M |
| 4,098,768 | 7/1978 | Hermans | 528/337 |

FOREIGN PATENT DOCUMENTS 148400 9/1962 U.S.S.R. .

*Primary Examiner*—Harold D. Anderson
*Attorney, Agent, or Firm*—Browdy and Neimark

[57] ABSTRACT

The present invention relates to novel aromatic and araliphatic polymers and copolymers based on phosphoric acid and thiophosphoric acid amides, esters and thioesters, to monomers for the production of these and to various products prepared from such polymers and copolymers, such as films, membranes, fibers and shaped objects.

19 Claims, No Drawings

POLYAMIDE FROM AROMATIC PHOSPHORUS CONTAINING DIAMINE

RELATION TO OTHER APPLICATIONS

The present application is a continuation-in-part application of U.S. Patent Application Ser. No. 652,812, filed Jan. 27, 1976, the entire contents of which are hereby incorporated by reference.

FIELD OF THE INVENTION

The present invention relates to novel polymers and copolymers, and more particularly to aromatic and araliphatic polymers and copolymers based on phosphoric acid and on thiophosphoric acid. The invention further relates to monomers, which are novel, and which are the starting materials for the preparation of the novel polymers and copolymers. The invention further relates to various products produced from such polymers and copolymers, namely to films, membranes, fibers and shaped objects prepared from such polymers and copolymers. One of the outstanding properties of the novel products is their stability at elevated temperatures.

Hitherto some phosphorous-containing polyamides were reported. One class of such polymers contains phosphorus atoms directly attached to an aromatic nucleus:

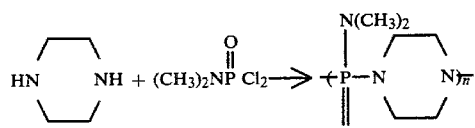

see Ger. Offen. No. 1,947,339; Chem Abstr. 73, 67213.

Phenyl phosphonic amide-containing polymers of the following formula were also prepared:

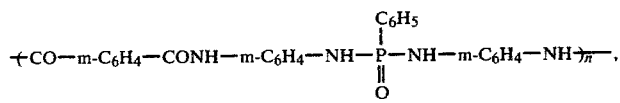

see Ger. Offen. No. 2,062,774; Chem. Abstr. 77, 127227.

Non-aromatic phosphoric triamides were prepared either by reaction of diamines with hexamethylphosphoric triamide, see (U.S. Pat. No. 3,546,141, 1970), or by the following reaction:

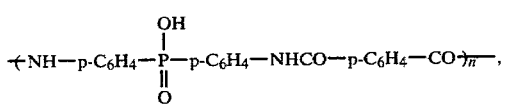

see Jagur et al, Macromol. 3, 98.

No fully aromatic poly(phosphoric amides) were reported to date. Such polymers offer a unique combination of physical and chemical properties as described below.

The present invention relates to novel polymers of the general formula I:

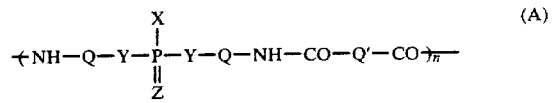

wherein
X designates —NHAr″, —N(R)Ar″, —NRR′, —NHR, —OR, —OAr″, or SR,
Y designates —O—, —NH—, —S—, or —N(CH$_3$)—,
Z designates =O or =S,
Q, Q′ and Q″ are Ar, Ar′ or alkylene or aralkylene of C$_4$ to C$_{10}$,
Ar and Ar′ designate p-C$_6$H$_4$, m-C$_6$H$_4$, R″C$_6$H$_3$,

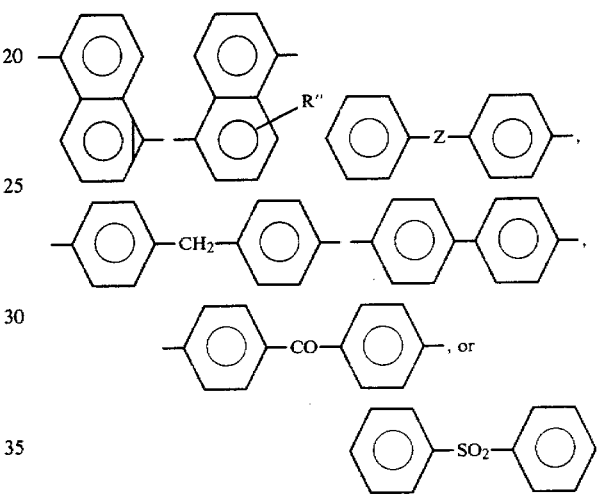

which
Q and Q″ may be identical or different,
Ar″ designates —C$_6$H$_5$, or —RC$_6$H$_4$,
R designates —CH$_3$, —C$_2$H$_5$, or —n—C$_3$H$_7$,
R′ designates —CH$_3$, —C$_2$H$_5$, or —n—C$_3$H$_7$, and
R″ designates —CH$_3$, —C$_2$H$_5$, —n—C$_3$H$_7$, —OCH$_3$, —OH, —COOH, or —COOR, wherein R is as defined above,
and to novel polymers of the Formula (II)

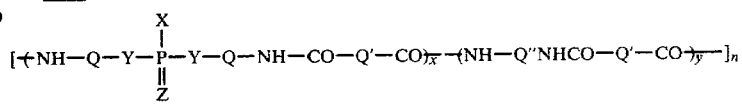

wherein Q, Q′, Q″, X, Y, Z are as defined above, wherein x and y are each an integer of from 1 to 5, n is an integer of from 50 to 200, and the polymer may contain different moieties of the type defined in the second parentheses;

a process for preparing such polymers and copolymers, and to products prepared from such polymers and copolymers, and more specifically fibers, films, membranes, shaped objects and devices based on such membranes and monomers for the production of same.

The novel polymers of the present invention are prepared according to the following reaction scheme:

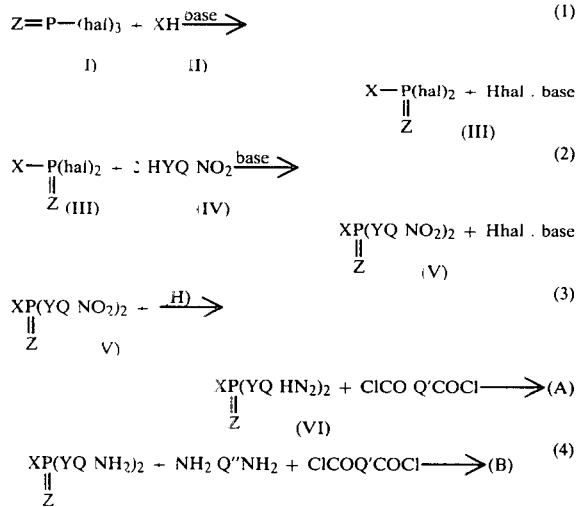

wherein hal designates a halogen selected from chlorine and bromine.

Suitable oxyhalides are phosphoryl chloride and phosphoryl bromide; a suitable phosphorus thiohalide is thiophosphoryl chloride.

Suitable nucleophiles for the reaction with the oxyhalides or thiohalides are amines such as for example, aniline, naphthylamine, alkylamines, alcohols, such as for example alkanols, i.e. methanol, ethanol, propanol, butanol, iso-propanol etc. phenolic compounds such as According to a preferred embodiment of the invention, the reaction between the oxyhalide or the thiohalide and the nucleophile is effected at a ratio of from 1:2 up to 1:4 molar ratio, and at a temperature in the range of 0° C. to about 30° C. The condensation of the phosphoric dichloride III with the aromatic nucleophile is effected at about 10° C. to about 110° C., preferably in a solvent such as ethyl acetate, with or without an acid acceptor such as pyridine. The preferred molar ratio being 2:1 to 4:1.

The polymerization of the diamine monomer is preferably effected by solution polycondensation in a solvent such as N,N-dimethylacetamide, hexamethylphosphoramide, N-methylpyrrolidone, etc, at about −30° to about 30° C.

A phosphorus oxyhalide or thiohalide (I) (such as $POCl_3$, $PSCl_3$) is treated with a suitable nucleophile (II) (e.g. amine, alcohol, phenol) so as to yield the corresponding monocondensation product of Formula (III), namely a N-phenyl-phosphoramide dichloride; phenyl phosphate dichloride, etc. This product (III) is then condensed with 2 equivalents of a nitroaromatic nucleophile (IV) (e.g. nitroaniline, nitrophenol). The product of this condensation, (V) is then reduced (e.g. by catalytic hydrogenation) to yield the diamine monomer (VI). The latter is then polymerized either with an aromatic diacid dichloride to yield polymer (A) or with an additional aromatic diamine and a diacid dichloride to yield polymer (B). In this manner high polymers are obtained ($N_{inh}=1.0$–$2.0$) which are highly flame resistant. Strong films, fibers and other objects may be prepared from them.

As a specific example of general Scheme I the preparation of 3,3′-diamino-N,N′,N″-triphenylphosphoric triamide and its polymerization are described in Scheme II,

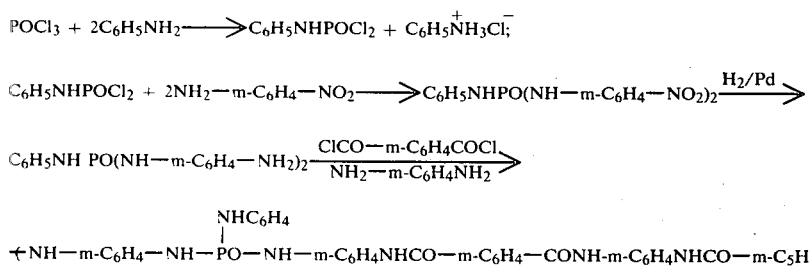

phenol, p-dimethylaminophenol, methoxyphenol, naphthol, and thiols such as thioalkanes.

Suitable nitroaromatic nucleophiles are, for example, nitroanilines, nitroaminonaphthalenes, and nitroaminobiphenyls.

Suitable aromatic diacid dichlorides are, for example,

Many of these polymerizations result in solutions from which strong fibers or films may be cast or fibers may be spun. Membranes prepared from these solutions exhibit an extraordinarily high ratio of urea to salt rejection, e.g. 95.0/96.5 for a membrane prepared from the polymer

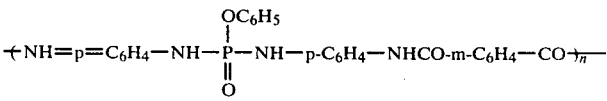

isophthaloyl chloride, terephthaloyl chloride, isophthaloyl bromide, benzophenone dicarboxylic acid chloride, p,p-biphenyl dicarboxylic acid chloride, etc.

Suitable diamines for preparing the copolymers, are for example, a phenylenediamine, p-phenylene diamine, diamino-p,p′-biphenyl, 1,6-diaminonaphtholene, etc.

and 99.2 for a membrane prepared from the polymer of the formula

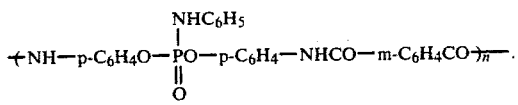

As expected the polymers posses very high flame resistance, e.g. the limiting oxygen index of a membrane made of polymer VII above is 46.9% whereas that of a similar membrane prepared from an aromatic polycarboxamide is 29.2%.

Many of the polymers are heat resistant as evident from their stability at temperatures as high as 300°–400° C., depending on the particular structure; most of the polymers lose only 40% to 50% of their weight during 2 hours at 650° C.

EXAMPLE 1

Preparation of Polymer

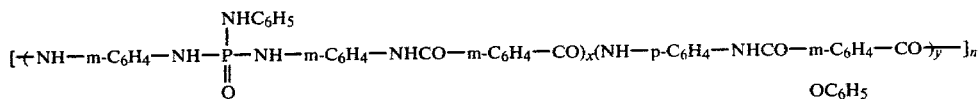

Phosphorous oxychloride is treated with 2 equivalents of aniline in dry benzene at room temperature. The product, N-phenyl phosphoric amide dichloride, crystallizes upon partial evaporation of the solvent. Condensation of the product with m-nitroaniline is carried out in pyridine at 60° C. The product is precipitated in an HCl-ice mixture and is recrystallized from ethanol-water.

| | | |
|---|---|---|
| M.P. = 209°–210° C., | Calculated: | C = 52.30, H = 3.87% |
| | Found: | C = 52.69, H = 4.82% |

It is then hydrogenated in an autoclave at 50 atm, at ambient temperature, over Pd/C. The diamine obtained

| | | |
|---|---|---|
| M.P. = 208°–209° C.: | Calculated: | C = 61.18, H = 5.71% |
| | Found: | C = 61.05, H = 5.77% | is copolymerized with m-phenylenediamine and isophthalic acid dichloride in N,N-dimethylacetamide at −20° C. The product is of the formula given above, inherent viscosity was 0.5 dl/g. Films, membranes or fibers are prepared directly from the polymerization mixture after standing for 24 hours. Other objects may be obtained from the polymer by conventional methods.

For example, skinned reverse osmosis membranes were prepared by a conventional technique from a 15% (w/v) solution of the above polymer in N,N-dimethylacetamide. The preparation was as follows: the solution was cast using a doctor-knife on a flat plate, evaporation of the solvent during 3–10′ at 90° C. at 10 mm/g, followed by coagulation in cold water. The membranes exhibited a salt rejection of 96% and a urea rejection of 94% and a water flux of 3 gallon per square foot per day (gfd) at a pressure of 50 atmospheres. The Oxygen Index measured on a sheet of membrane of 0.1 mm thickness was 46.9%. The distribution coefficient of NaCl between a 5% aqueous solution and a polymer film was found to be 0.5 (the distribution coefficient for aromatic carboxamide films previously measured was 0.17). The diffusivity of salt in a polymer film 0.05 mm thickness was found to be very low, namely $3.5 \times 10^{-12}$ cm$^2$/sec. The polymer is stable up to 400° C. during 2 hours.

EXAMPLE 2

Preparation of Polymer

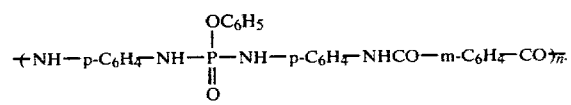

Phenyl phosphate dichloride

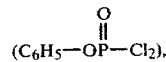

is obtained by the reaction of phenol with phosphoric oxychloride. It is condensed with 2 equivalents of p-nitroaniline as in Example 1. Reduction of the condensation product is accomplished by catalytic hydrogenation at 4 atmospheres. The diamine obtained,

| | | |
|---|---|---|
| Calculated: | C = 61.01, | H = 5.40 |
| Found | C = 61.15, | H = 5.50 | is polymerized with isophthaloyl chloride in N,N-dimethylacetamide at 35° C. The inherent viscosity of the polymer was 1.1 dl/g. Salt rejection of a membrane prepared from a 20% (w/v) polymer solution was 97% and urea rejection was 95%. The polymer is stable at 300° C. and loses 44% of its weight when heated to 600° C. during 2 hours.

EXAMPLE 3

Preparation of Polymer

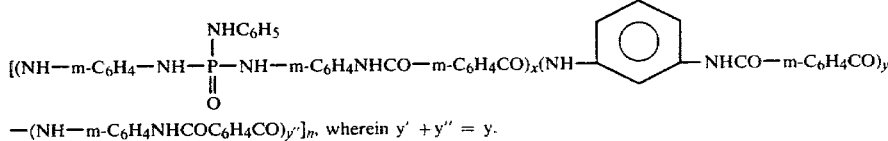 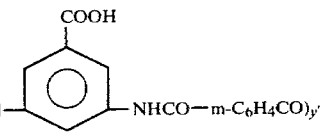

$-(NH-m-C_6H_4NHCOC_6H_4CO)_{y''}]_n$, wherein $y' + y'' = y$.

3,3′-Diamino-N,N′,N″-triphenylphosphoric triamide prepared as described in Example 1 is copolymerized with phenylene diamine and 3,5-diaminobenzoic acid in a molar ratio of 1:8:1 respectively, by polycondensation with isophthaloyl chloride as described in Example 1. A clear viscous solution is obtained from which tough films and fibers may be prepared. The inherent viscosity is 1.3 dl/g and salt rejection of a 0.1 mm thick membrane cast from a polymer solution is 97% while urea rejection is 92%.

EXAMPLE 4

Preparation of Polymer

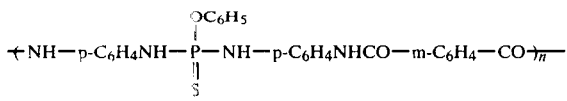

Phenol is treated with an excess of thiophosphoryl chloride (at reflux) to yield phenyl thiophosphoryl dichloride

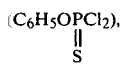

and this product was condensed with p-nitroaniline and hydrogenated as set out in Example 1. The corresponding polymer is obtained by polycondensation with isophthaloyl chloride as in Example 2. The inherent viscosity was 0.9 dl/g.

EXAMPLE 5

Preparation of Polymer

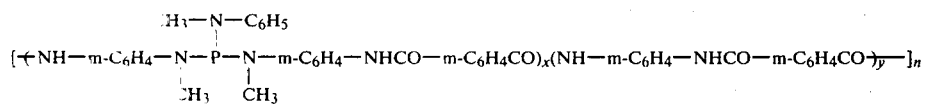

3,3'-Dinitro-N,N',N''-triphenylphosphoric triamide is permethylated by a phase transfer reaction. To the triamide is dioxane is added excess methyl iodide and an aqueous solution containing 50% (w/v) NaOH and 0.3 equivalents of tetrabutyl ammonium bromide. The N,N'N''-methylated product is obtained by vigorous stirring and heating at 40° C. By hydrogenation and polymerization, as in Example 1, a polymer is obtained which is more resistant to hydrolytic conditions than the polymer of Example I, thus this polymer withstands treatment with 1 N HCl and 60° for 24 hours whereas the polymer of Example I is partially hydrolized, under these conditions. Inherent viscosity 0.6 dl/g.

EXAMPLE 6

Preparation of Polymer

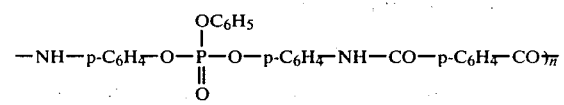

N-phenyl phosphoric amide dichloride is treated at 80° C. during 5 hours with an excess of p-nitrophenol in pyridine. The product is hydrogenated and the resulting diamine is polymerized as set out in Example 1. The polymer obtained has an inherent viscosity of 1.0 dl/g. Membranes of extremely high (>99%) urea rejection may be obtained from the polymer. The polymer is stable at 300° C. and loses 48% of its weight when heated during 2 hours at 660° C.

EXAMPLE 7

Preparation of Polymer

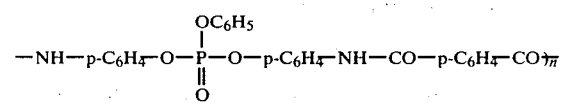

Phenyl phosphate dichloride is treated at 60° C. during 12 hours with an excess of p-nitrophenol in pyridine. The product is hydrogenated and the resulting diamine is polymerized with terephthaloyl chloride as set out in Example 2. Intrinsic viscosity: 1.2.

EXAMPLE 8

Preparation of Polymer

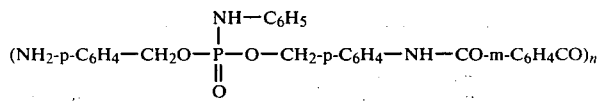

N-phenyl phosphoric amide dichloride is condensed with p-nitrobenzyl alcohol, essentially as set out in Example 7. The product is hydrogenated and polymerized as set out in Example 2.

EXAMPLE 9

Preparation of Polymer

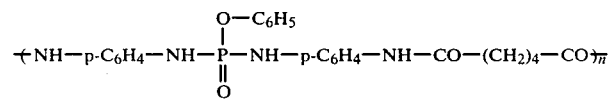

The diamine monomer obtained in Example 2 is polymerized with adipyl chloride in the manner set out in Example 2. Intrinsic viscosity is 0.7.

We claim:

1. A polymer consisting essentially of the following repeating unit:

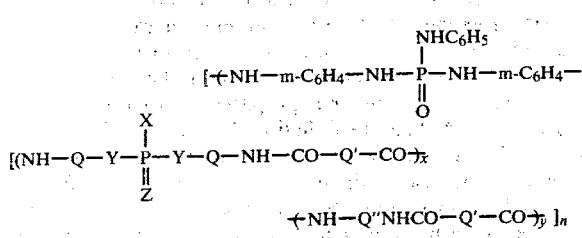

$$[(NH-Q-Y-\underset{\underset{Z}{\|}}{P}-Y-Q-NH-CO-Q'-CO)_x$$

$$-(NH-Q''NHCO-Q'-CO)_y]_n$$

wherein

X designates —NHAr, N(R)Ar, —NRR', NHR, —OR, —OAr, or SR,

Y designates —O—, —NH—, —S—, or —N(CH$_3$)—,

Z designates =O or =S,

Q, Q' and Q" designate p-C$_6$H$_4$, m-C$_6$H$_4$, R"C$_6$H$_3$,

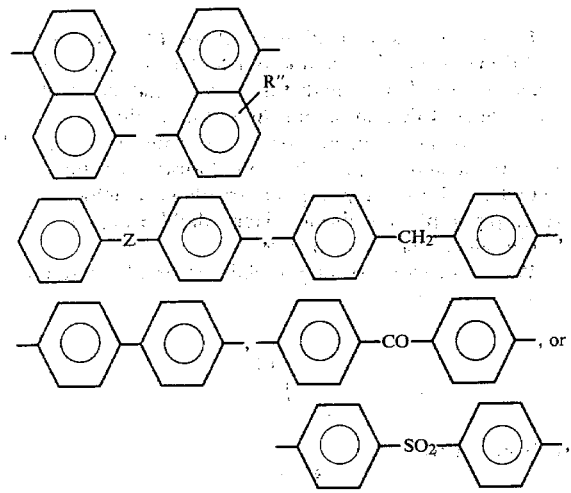

which

Q, Q', and Q" may be identical or different,

Ar designates —C$_6$H$_5$, or RC$_6$H$_4$,

R designates —CH$_3$, C$_2$H$_5$, or —n—C$_3$H$_7$,

R' designates —CH$_3$, C$_2$H$_5$, or —C$_3$H$_7$, and

R" designates —CH$_3$, —C$_2$H$_5$, n—C$_3$H$_7$, —OCH$_3$, —OH, —COOH or —COOR, wherein R is as defined above, x is an integer of from 1 to 5, y is zero or an integer of 1 to 5, and n is an integer of from 50 to 200; wherein the repeating portions within the right-hand parentheses of said re- peating unit when y is greater than 1 are alike or different.

2. A polymer according to claim 1 of the formula

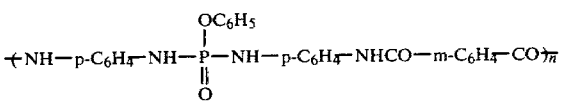

wherein y is an integer of from 1 to 5 and x and n are as defined in claim 1.

3. A polymer according to claim 1, of the formula

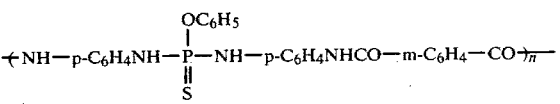

wherein n is as defined in claim 1.

4. A polymer according to claim 1, of the formula

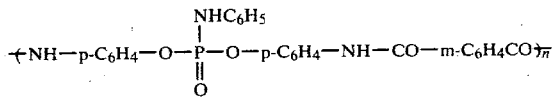

wherein n is as defined in claim 1.

5. A polymer according to claim 1, of the formula $$-(NH-p-C_6H_4-O-\underset{\underset{O}{\|}}{\overset{NHC_6H_5}{P}}-O-p-C_6H_4-NH-CO-m-C_6H_4CO)_{\overline{n}}$$

wherein n is as defined in claim 1.

6. A polymer according to claim 1, being the polymerization product of an aromatic phosphoric acid ester diamine or thiophosphoric ester amide diamine with an aromatic diacid dichloride.

7. A polymer according to claim 1, being the polymerization product of an aromatic phosphoric triester diamine or thiophosphoric triester diamine with an aromatic diacid dichloride.

8. A polymer according to claim 1, being the polymerization product of an aromatic phosphoric triamide diamine with a diamine aromatic hydrocarbon and an aromatic diacid dichloride.

9. A polymer according to claim 1, of the formula

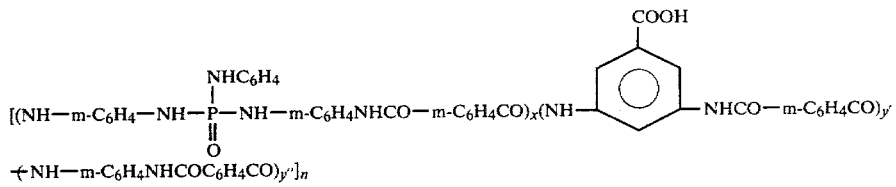

wherein y' and y" are integers which added together total y, y is an integer of from 1 to 5, and x and n are as defined in claim 1.

10. A polymer according to claim 1, of the formula

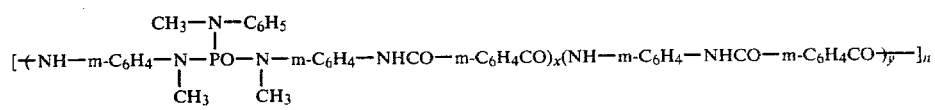

wherein y is an integer of from 1–5 and x and n are as defined in claim 1.

11. A polymer according to claim 1, in the form of a membrane, and having the formula

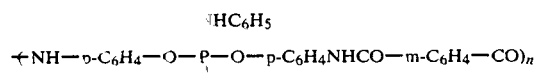

wherein n is as defined in claim 1.

12. A polymer in accordance with claim 1, in the form of a membrane, film, fiber or other shaped product.

13. A polymer according to claim 1, in the form of a membrane and having the formula

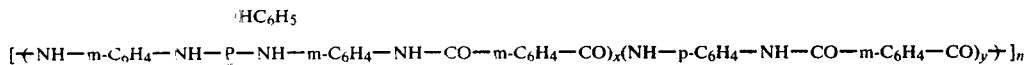

wherein y is an integer of 1 to 5 and x and n are as defined in claim 1.

14. A process for producing the polymer defined in claim 1, wherein y is zero, comprising polymerizing a diamine monomer of the formula $XP(=Z)(YQNH_2)_2$ with an aromatic diacid dichloride of the formula $ClCO—Q'—COCl$.

15. A process in accordance with claim 14 wherein said diamine monomer is prepared by treating a phosphorus oxyhalide or thiohalide ($POhal_3$ or $PShal_3$) with a nucleophile to yield a N-phenyl-phosphoramide or phosphoric ester dihalide, or thiophosphoramide or thiophosphoric ester dihalide; condensing this reaction product with 2 equivalents of a nitro-aromatic nucleophile of the formula $HYQNO_2$, to yield a compound of the formula $XP(=Z)(YQNO_2)_2$; and reducing by catalytic hydrogenation to the diamine monomer.

16. A process for producing the polymer defined in claim 1, wherein y is an integer of 1 to 5, comprising polymerizing a diamine monomer of the formula $XP(=Z)(YQNH_2)_2$ with an additional aromatic diamine of the formula $NH_2Q''NH_2$ and with an aromatic diacid dichloride of the Formula $ClCO—Q'—COCl$.

17. A process in accordance with claim 16 wherein said diamine monomer is prepared by treating a phosphorus oxyhalide or thiohalide ($POhal_3$ or $PShal_3$) with a nucleophile to yield a N-phenyl-phosphoramide or phosphoric ester dihalide, or thiophosphoramide or thiophosphoric ester dihalide; condensing this reaction product with 2 equivalents of a nitroaromatic nucleophile of the formula $HYQNO_2$, to yield a compound of the formula $XP(=Z)(YQNO_2)_2$; and reducing by catalytic hydrogenation to the diamine monomer.

18. A process according to claim 14, wherein the additional aromatic diamine is selected from the group consisting of phenylene diamines, naphthalene diamines and biphenyl diamines, and the aromatic diacid dichloride is a member selected from the group consisting of isophthalic and terephthalic acid chloride, p,p'-biphenyl diacid dichloride, p,p'-diphenylmethane diacid dichloride, p,p'-diphenylsulfone diacid dichloride, and 4,6-naphthalene diacid dichloride.

19. A process according to claim 15 or 17 wherein the ratio of $HYQNO_2$ to

is from 2:1 to 4:1.